(12) United States Patent
Luther et al.

(10) Patent No.: US 6,595,954 B1
(45) Date of Patent: Jul. 22, 2003

(54) INSERTION NEEDLE AND SOFT CATHETER SYSTEM WITH TIP PROTECTOR

(75) Inventors: Ronald B. Luther, Newport Beach, CA (US); Charles W. Dickerson, Tustin, CA (US)

(73) Assignee: Luther Research Partners, LLC, Irvine, CA (US)

( * ) Notice: Subject to any disclaimer, the term of this patent is extended or adjusted under 35 U.S.C. 154(b) by 0 days.

(21) Appl. No.: 09/523,878

(22) Filed: Mar. 13, 2000

(51) Int. Cl.[7] ................................................. A61M 5/32
(52) U.S. Cl. ........................................ 604/110; 604/198
(58) Field of Search ............................. 604/110, 164.08, 604/198

(56) References Cited

U.S. PATENT DOCUMENTS

| | | |
|---|---|---|
| 4,964,854 A | 10/1990 | Luther |
| 5,215,525 A | 6/1993 | Sturman |
| RE34,416 E * | 10/1993 | Lemieux .................... 604/198 |
| 5,419,766 A | 5/1995 | Chang et al. |
| 5,558,651 A | 9/1996 | Crawford et al. |
| 5,569,202 A | 10/1996 | Kovalic et al. |
| 5,611,781 A | 3/1997 | Sircom et al. |
| 5,662,610 A | 9/1997 | Sircom |
| 5,688,249 A | 11/1997 | Chang et al. |
| 5,718,688 A | 2/1998 | Wozencroft |
| 6,004,294 A | 12/1999 | Brimhall et al. |
| 6,379,333 B1 * | 4/2002 | Brimhall et al. ............ 604/110 |

FOREIGN PATENT DOCUMENTS

| | | |
|---|---|---|
| EP | 0 475 375 A1 | 3/1992 |
| EP | 0 475 375 B1 | 12/1994 |
| EP | 0 645 159 A1 | 3/1995 |
| EP | 0 747 083 A2 | 12/1996 |
| EP | 0 791 370 | 8/1997 |
| EP | 0 830 872 | 3/1998 |
| EP | WO 00/06226 | 2/2000 |
| WO | WO 99/08742 | 2/1999 |

OTHER PUBLICATIONS

"The World's First Passive Safety IV Catheter"; B. Braun; Introcan safety; Jul. 1999.
"The New Generation with Optimized Puncture Characteristics"; B. Braun; Vasofix Braunule; Mar. 6, 1999.
Abstract of EPO Publication No. 0554841, Published Nov. 8, 1992.
PCT International Search Report dated Sep. 14, 2001 for PCT/US01/07984.

* cited by examiner

Primary Examiner—Gerald A. Michalsky
(74) Attorney, Agent, or Firm—Knobbe, Martens, Olson & Bear LLP

(57) ABSTRACT

A catheter and insertion needle assembly comprising a catheter having a catheter hub and an insertion needle for disposition within the catheter and catheter hub. The assembly further comprises a shielding means comprising a generally cylindrical sleeve and means for locking the needle within the shielding means so as to safely enclose the tip of the needle to prevent exposure to clinicians. The shielding means preferably includes a retainer ring externally positioned thereon, wherein the retainer ring is configured to engage a corresponding retainer depression in an internal wall of the catheter hub. The locking means includes a locking ring on the exterior of the needle and a short, generally cylindrical, rigid insert disposed tightly within the interior of the shielding means. The insert has a slight decreasing taper at its proximal end and comprises cantilevered segments that may be biased outward to form a spring to permit movement of the locking ring in one direction, but not the other. The rigid insert is preferably positioned so that, when the insertion needle and locking ring are withdrawn proximally through the insert, the locking ring may be axially restricted between the insert and the proximal end of the shielding means. Further pulling would dislodge the needle and shielding means from the catheter hub, leaving the tip of the needle shielded from inadvertent contact.

4 Claims, 3 Drawing Sheets

INSERTION NEEDLE AND SOFT CATHETER SYSTEM WITH TIP PROTECTOR

FIELD OF THE INVENTION

The present invention relates generally to a vascular catheter and insertion needle assembly and, more specifically, to an assembly that includes a tip protector that safely shields the insertion needle tip when withdrawn from the catheter.

BACKGROUND OF THE INVENTION

Catheters are well known for being used to fluidly communicate with the vascular system of a patient in a minimally invasive procedure, whether to withdraw fluids from the patient or to infuse fluids into the patient. Catheters are generally short thin flexible tubes that are open at a distal end and secured within a hub at a proximal end. The hub serves as a quick disconnectable mechanical connector between the catheter and a delivery tube extending, for example, from a liquid source.

One typical catheter is an over-the needle style catheter that requires an insertion needle passing therethrough to penetrate the patient's skin and advance the catheter into the patient's vascular system. The needle comprises a beveled distal end to facilitate piercing the patient's skin and a proximal end having a hub for handling purposes. When the distal end of the catheter is in place within the patient's vascular system, the insertion needle may be withdrawn, leaving the catheter hub exposed at the proximal end to connect to a delivery tube. Pressure applied by the clinician to the blood vessel occludes blood flow, permitting the clinician to connect the catheter hub to the delivery tube either to withdraw blood or to infuse fluids into the patient.

Traditionally, once the insertion needle was withdrawn from the catheter, the sharp distal tip of the needle was left exposed to the clinician until properly disposed. This put the clinician at risk of being inadvertently "stuck" by the needle, causing injury and, more critically, to inadvertent internal exposure to the patient's blood. Where a patient suffers from a communicable disease, particularly Acquired Immunosuppressive Deficiency Syndrome (AIDS), that risk is unacceptable. Despite being aware of the need to properly handle blood contaminated needles, under certain circumstances, including emergency situations or inattention, inadvertent sticks of the insertion needle into the clinician still occur.

To address the problem, efforts have been made to shield the exposed tip of the needle when it is withdrawn from the patient. For example, U.S. Pat. No. 6,004,294 to Brimhall et al. discloses a needle shield that includes a leaf spring that engages a shoulder formed from a tapered section of the insertion needle to prevent axial movement of the insertion needle after it has been withdrawn to a certain position. While effective at shielding the needle tip, the Brimhall device is a somewhat complex arrangement of features that results in a more expensive and cumbersome assembly that can be misused. A simpler passive and more efficient tip protecting assembly is desired.

SUMMARY OF THE INVENTION

The present invention is a catheter and insertion needle assembly that overcomes the deficiencies of the prior art by providing a simpler, entirely passive, and more effective means for safely shielding the distal tip of the insertion needle as it is withdrawn from the catheter. The result is that the clinician may use the assembly without risk of inadvertent injuries and, more importantly, without risk of contracting a communicable disease from the patient undergoing treatment. The present invention is a catheter and insertion needle assembly that comprises a catheter with catheter hub, an insertion needle, means for shielding the tip of the needle, means for locking the needle within the shielding means and means for removably locking the shielding means within the catheter hub. Specifically, the preferred embodiment of the assembly comprises a soft resilient catheter that has preferably been treated at its distal end to create a relatively hard catheter tip for facilitating engagement with a patient, as described in co-pending applications, Ser. No. 09/146,451, now U.S. Pat. No. 6,500,157, and Ser. No. 09/524,039, entitled Hard Tip Over-The-Needle Intravenous Catheter and filed on Mar. 13, 2000, which are incorporated herein in their entirety by reference. The catheter further preferably includes an internal shoulder near the distal end thereof that may be provided by the techniques described in the referenced application.

The shielding means comprises a shield or tip protector comprising a generally cylindrical tube configured so as to be disconnectably disposed within the catheter hub. The tip protector preferably includes a retainer ring externally positioned thereon, wherein the retainer ring is configured to engage a corresponding retainer depression in an internal wall of the catheter hub. When the retainer ring is engaged with the retainer depression, the tip protector remains securely positioned within the catheter hub. When the retainer ring is not engaged with the retainer depression, the tip protector may be moved axially within the catheter hub. The proximal end of the tip protector has a small opening that is just large enough to permit the passage of the insertion needle through but small enough to preclude passage of the locking ring. The distal end has an internal diameter sufficiently large to permit passage of both the needle and the locking ring.

The insertion needle comprises a uniform diameter cannula that has a beveled tip at its distal end. The needle is sized to be axially disposed within the catheter and catheter hub. The means for locking the needle tip within the tip protector comprises in part a locking ring securely disposed over the needle near the distal end of the needle. The locking ring is positioned on the needle so as to permit the needle tip to project through the catheter sufficiently to provide effective penetration of the needle and catheter into a patient's vascular system. The locking ring is also preferably positioned on the needle so as to abut the internal shoulder of the catheter when the insertion needle is fully inserted within the catheter.

The means for locking the needle tip within the tip protector further comprises an insert comprising a short, generally cylindrical, metal, collar disposed securely within the interior of the tip protector. The insert is intended to be immovable within the tip protector. The insert has a slight decreasing taper at its proximal end so that the interior diameter of the proximal end is large enough to permit the passage therethrough of the insertion needle but small enough to preclude easy passage of the locking ring, although it may be forced through, as explained below. The tapered end of insert is segmented into discrete cantilevered sections that may be biased outwardly when the locking ring is forced through the insert. It is intended that the metal insert be positioned within the tip protector so that, when the insertion needle and locking ring are withdrawn proximally and forcibly through the insert, the locking ring is restricted from further axial movement in either direction between the metal insert and the proximal end of the tip protector.

With the above arrangement, when the insertion needle is inserted within the catheter to its fullest extent, the locking ring abuts the internal shoulder of the catheter. The abutment helps to transfer forces from the needle to the catheter as the needle is pushed distally through the catheter and into the patient. The hard tip helps to advance the otherwise soft catheter into the patient's vascular system. When the insertion needle is withdrawn from the patient, it moves axially through the tip protector so that the locking ring forcibly passes through the spring actuating metal insert. The locking ring then becomes lodged between the metal insert and the proximal end of the tip protector, preventing further axially movement of the needle within the tip protector. At this point, the insertion needle is, in effect, locked in place. By exerting additional pulling force on the insertion needle in the proximal direction, the pressure of the locking ring against the proximal end of the tip protector forces the tip protector to disengage from the catheter hub. Continued pulling results in the insertion needle being fully withdrawn from the catheter and catheter hub with the distal tip of the insertion needle securely shielded by the tip protector against inadvertent sticks by clinicians.

The present invention may be described in more detail with reference to the following figures.

DETAILED DESCRIPTION OF THE PREFERRED EMBODIMENT

Figure 1:
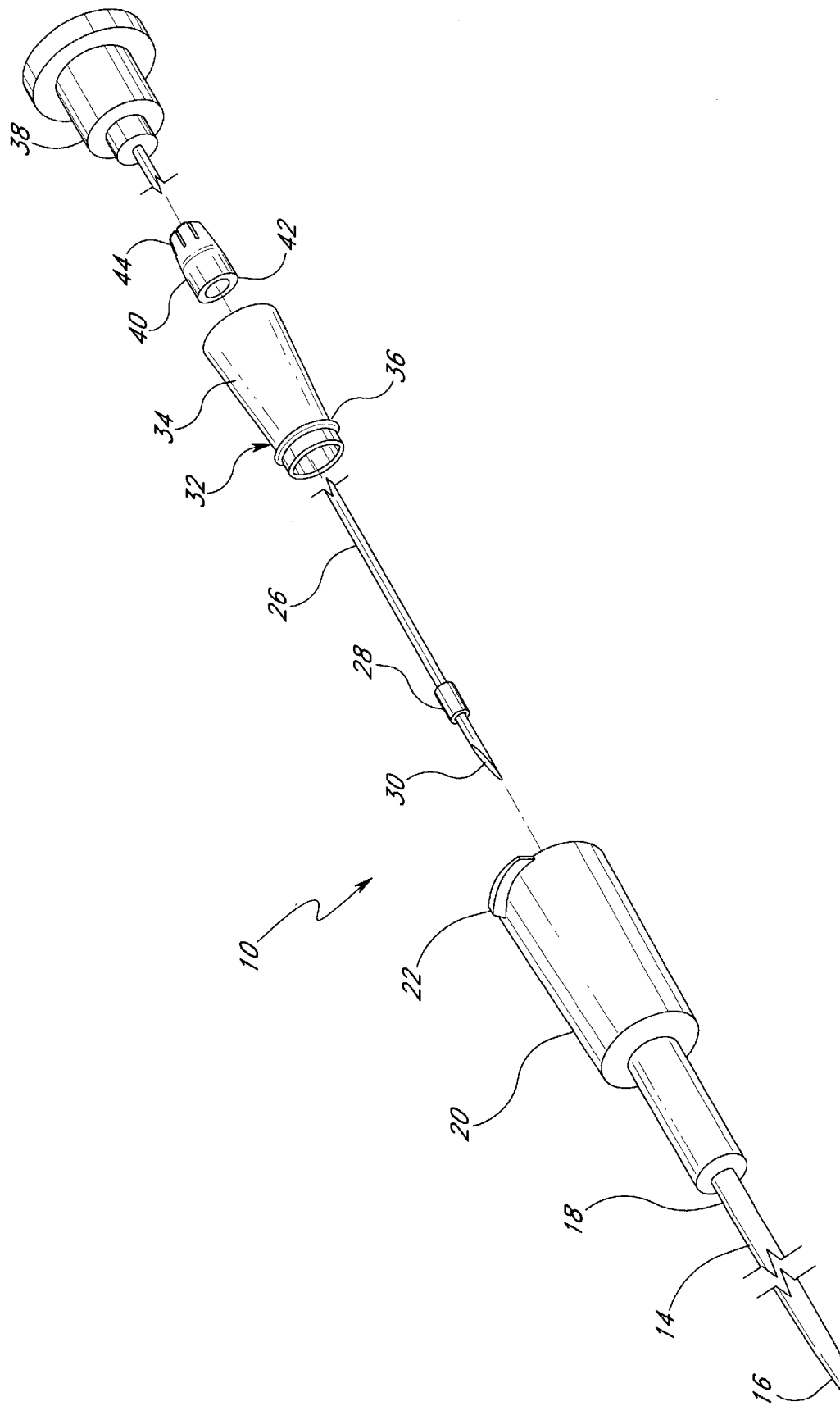
FIG. 1 is an exploded perspective view of the components of the catheter and insertion needle assembly.

Reference is now made to the figures wherein like parts are designated with like numerals throughout. Referring first to FIG. 1, the present invention is a catheter and insertion needle assembly 10 that generally comprises four main components, all of which are discussed in detail below: a catheter 14, an insertion needle 26, shielding means 32 for shielding the tip of the needle, and locking means for locking the needle within the shielding means, which in the preferred embodiment comprises a rigid insert 40.

The catheter 14 has a distal end 16, which is to be inserted into a patient, and a proximal end 18, which is sealably connected to a catheter hub 20. The catheter hub 20 has a luer fitting 22 for quick connection to a delivery tube (not shown). The catheter is preferably 1 to 6 inches long with a diameter in the range of 0.025–0.100 inches and is made of polyurethane or similarly durable thermoplastic material. Preferably, the hardness of the catheter is less than 85 on the Shore A hardness scale and, more preferably, about 70A. The soft material catheter is preferably treated at its distal end 16 to be harder than the rest of the catheter, resulting in a tip hardness of greater than about 90A and, more preferably, about 99A. The soft material catheter with hardened tip may be made as described more fully in co-pending application Ser. No. 09/146,451, now U.S. Pat. No. 6,500,157, and Ser. No. 09/524,039, entitled Hard Tip Over-The-Needle Intravenous Catheter and filed on Mar. 13, 2000, which are incorporated in their entirety herein by reference. The interior of the catheter 14 preferably has an internal shoulder (not shown) than may be beveled or stepped, as is discussed in more detail in association with FIGS. 4A–4D. The configuration of the internal shoulder also depends upon whether the catheter is made of generally soft material, with or without a hardened tip, or is made of a generally harder material, where treatment of the tip may not be necessary.

The catheter 14 is an over-the-needle style catheter that requires an insertion needle to insert the catheter into the patient's vascular system. In that regard, the assembly 10 further comprises an insertion needle 26, which includes a locking ring 28 secured to the exterior thereof. The locking ring 38 is part of the means for locking the needle within the shielding means 32. As explained below, the locking ring interfaces with other components, including the insert 40, to lock the needle within the shielding means. In lieu of a ring, a tab or a plurality of tabs that are made integral with or secured to the needle may be used.

The insertion needle 26 is sized to fit within the catheter 14 and has a beveled tip 30 at its distal end and a flashback chamber 38 at its proximal end. The chamber 38 includes a hydrophobic plug at the exposed end that permits air to pass therethrough while precluding the passage of blood or other fluid. Preferably, the needle has a relatively uniform diameter of about 0.028 inches in diameter, although the invention described herein would apply to an insertion needle of any diameter. The locking ring 28 is preferably about 0.003 inches thick and may be made integrally with the needle 26 or, preferably, is heat shrunk around or securely adhered to the needle 26 as a discrete component. In one embodiment, the locking ring 28 is secured to the needle 26 via a spot weld applied at least to the edge of the locking ring 28 so as to result in a beveled surface contour. However it is applied to the needle, the locking ring's distal edge preferably has a surface contour that corresponds to the interior contour of the internal shoulder of the catheter 14, as described below.

To address the risk of inadvertent contact with the exposed insertion needle, the shielding means comprises a tip protector 34 that preferably comprises a generally cylindrical sleeve that includes an external retainer ring 36 integral with or secured on the tip protector. The tip protector 34 has a closed proximal end (not shown) with an opening therein (also not shown) for passage of the insertion needle therethrough, as described more fully in association with FIGS. 4A–4D. The tip protector 34 is preferably made of semi-rigid plastic and is about 0.5 inch long, with an interior Luer dimension diameter. The retainer ring 36 projects about 0.006 inches from the exterior surface of the tip protector and is shaped to removably interlock with a retainer depression (not shown) in the interior of the catheter hub, as discussed further below.

Figure 3:
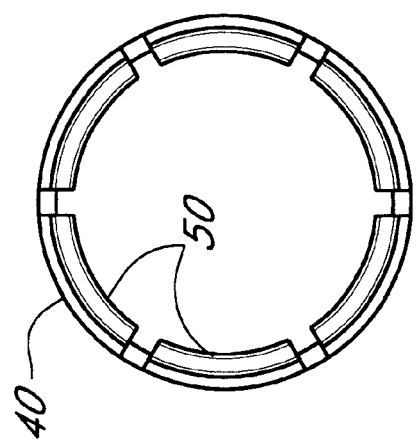
FIG. 3 is an end view of the metal insert of FIG. 3.
Figure 2:
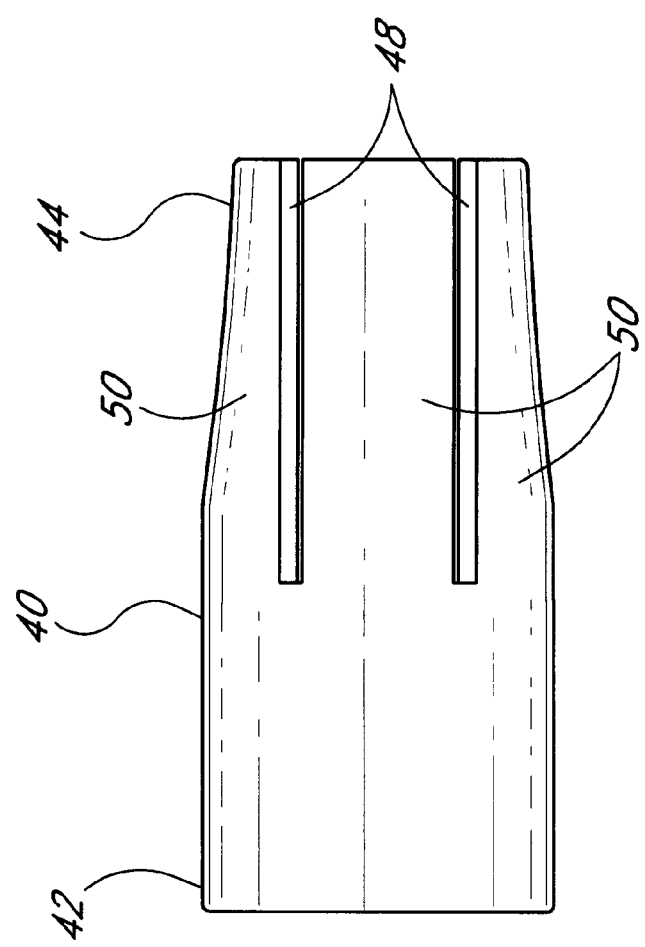
FIG. 2 is side view of the metal insert.

Still referring to FIG. 1, the means for locking the insertion needle within the tip protector further comprises spring means, which, in the preferred embodiment, comprises a rigid insert 40. The insert may be made of metal, such as stainless steel, or a sufficiently sturdy thermoplastic material, such as polycarbonate. The insert 40 comprises a cylindrically shaped collar that is of generally uniform diameter at a distal end 42 and is slightly tapered so as to have a decreasing diameter at a proximal end 44. Referring to FIGS. 2 and 3, the insert 40 is preferably about 0.25 inches long and has an interior diameter preferably of at least 0.032 inches at its distal end 42. The insert also preferably has an interior diameter at its proximal end no less than the diameter of the insertion needle and no greater than the diameter of the locking ring. In the preferred embodiment, the proximal interior diameter must be greater than 0.028 inches but less than 0.031 inches. As shown in FIG. 2, specifically, the proximal end 44 is tapered with a decreasing internal diameter. To permit spring biasing of the proximal end of the insert 40, longitudinal slots 48 are provided in the insert at radially spaced intervals to create cantilevered sections 50. The number of slots 48 required depends upon the wall thickness and the type of material used. For purposes of illustration only, the insert 40 is shown with six slots. The length of the slots should be selected so that the sections 50 may be biased outwardly by the force of the larger diameter locking ring 28 as it is pulled axially in the proximal direction. Once the locking ring 28 has passed through the insert 40, the cantilevered sections spring back, preventing the locking ring from moving backward in the distal direction through the insert. If the insert 40 is positioned properly within the tip protector 34, the locking ring 28 should end up positioned between the insert 40 and the proximal wall of the tip protector to prevent substantial movement in both directions, as discussed further below.

Figure 4A:
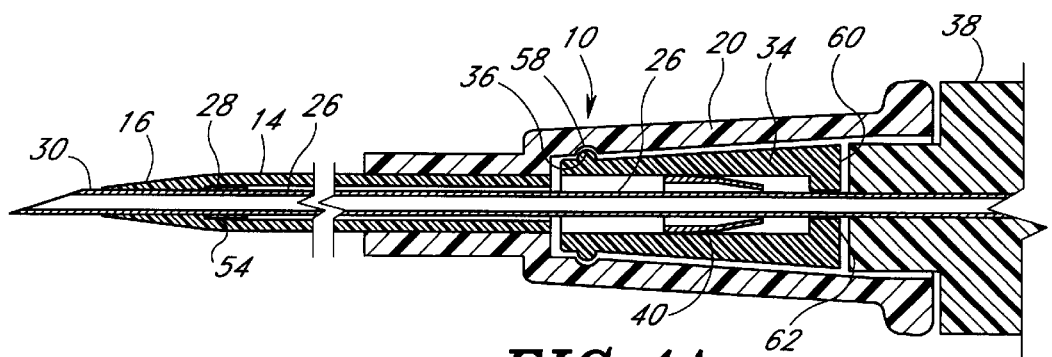
FIG. 4A is a cross section of the assembly showing the insertion needle fully inserted distally through the catheter.

Referring now to FIGS. 4A through 4D, the advantages of the present invention may be fully appreciated. It is contemplated that the assembly 10 be shipped assembled, as shown in FIG. 4A. Preferably, when the system is prepared for shipment to the end user, the distal end of the catheter 14 is enclosed by one of a number of well known disposable protective sheaths (not shown). When it is desired to utilize the present invention assembly to insert the catheter into a patient, the insertion needle 26 is advanced to its furthest distal position, as shown in FIG. 4A. At this position, the beveled tip 30 of the needle 26 projects distally from the distal end 16 of the soft material catheter. This permits the exposed needle tip to pierce the skin and blood vessel of the patient. At its most distal position, the locking ring 28 of the insertion needle 26 preferably abuts the internal shoulder 54 (shown more clearly in FIG. 4B). When the locking ring 28 has a stepped contour at its distal end, as shown, it is preferred that the internal shoulder 54 of the catheter 14 also have a stepped contour, to more efficiently transfer to forces.

Still referring to FIG. 4A, the tip protector 34 is removably locked within the interior of the catheter hub 20. The tip protector 34 is prevented from axial movement within the catheter hub 20 by locking means that comprises the retainer ring 36 of the tip protector and the retainer depression 58 (shown more clearly in FIG. 4D). It should be appreciated that, if desired, a retainer ring could be provided on the interior wall of the catheter hub and a retainer depression disposed on the exterior wall of the tip protector, with the same desired result. Other means for removably locking the shielding means (tip protector) within the catheter hub are also contemplated, including breakable tabs.

As shown in FIG. 4A, the exterior diameter of the insert 40 is almost identical to the internal diameter of the tip protector 34 so that the former is securely lodged within the tip protector sufficiently tight to prevent relative movement therebetween. Preferably the insert 40 is press fit into the tip protector by a process of heat shrinking the tip protector around the insert. If desired, the insert can be made with a detent that engages a corresponding depression in the interior of the tip protector to permit interlocking engagement that is not easily overcome by the forces exerted by the clinician during either insertion or withdrawal of the needle. Other means of accomplishing the interlocking engagement of the insert with the tip protector are also contemplated. However the insert is coupled to the tip protector, it is intended that the insert not be movable axially within the tip protector during normal use. The means for locking the needle 26 within the tip protector 34 further comprises a wall 60 at the proximal end of the tip protector with an opening 62 therein. The opening 62 has a diameter sufficiently large to permit passage of the needle 26 therethrough, but sufficiently small to prevent passage of the locking ring 28 therethrough.

Figure 4B:
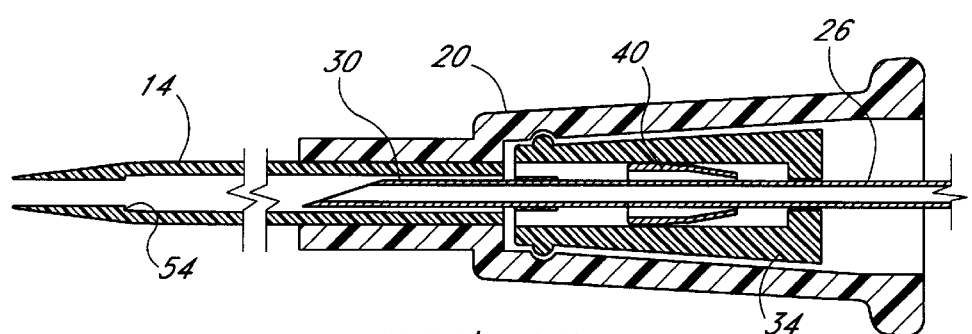
FIG. 4B is a cross section of the assembly of FIG. 2A showing the insertion needle partially withdrawn through the catheter.
Figure 4C:
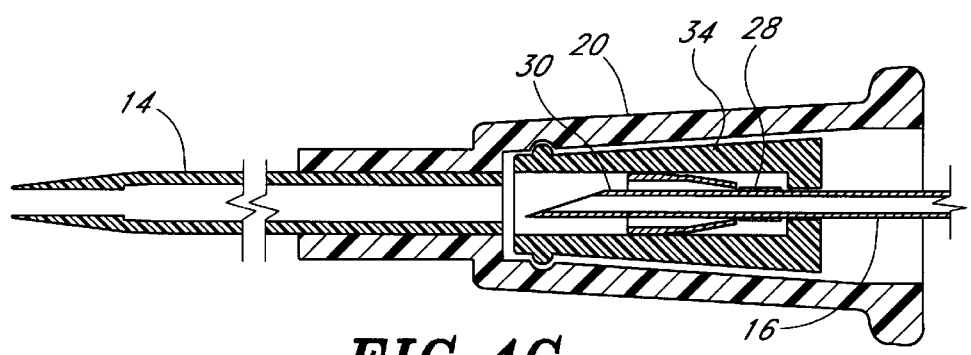
FIG. 4C is a cross section of the assembly of FIG. 2A showing the insertion needle locked within the tip protector.
Figure 4D:
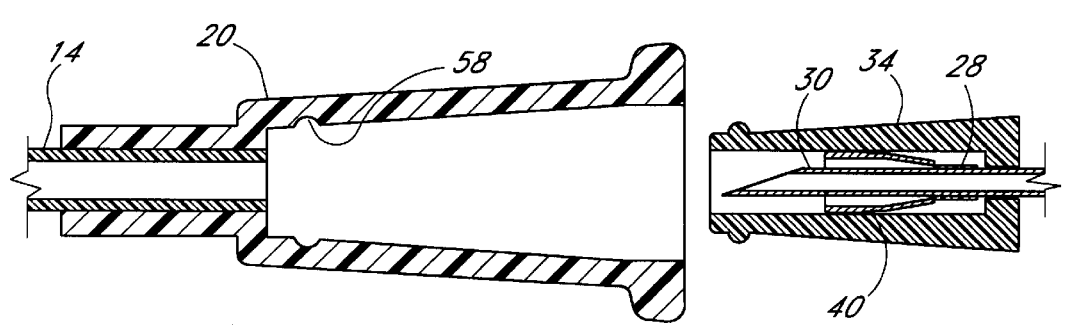
FIG. 4D is a cross section of the assembly of FIG. 2A showing the tip protector dislodged from engagement with the interior of the catheter hub.

After the distal end 16 of the catheter 14 has been inserted into the patient, the clinician may occlude the blood vessel for the time it takes to withdraw the insertion needle and connect the catheter hub 20 to a delivery tube. By pulling axially in the proximal direction on the end of the needle 32, the needle tip is withdrawn into the interior of the catheter 14 and into the catheter hub 20, as shown in FIG. 4B. Further proximal movement of the needle 26 brings the locking ring 28 into contact with and through the insert 40, as shown in FIG. 4C. The result is that the locking ring 28 become lodged between the proximal end of the insert and the proximal wall 60 of the tip protector. By doing so, the insertion needle 26 is prevented substantially from further axial movement, in either direction. Importantly, by securing the needle in this position, the tip 16 of the needle is completely housed within the interior of the tip protector 34. While there may be some residual room for the locking ring to move slightly back and forth, substantial movement of the needle is nonetheless prevented so that the tip of the needle can no longer project beyond the distal end of the tip protector.

Continued pulling on the needle 26 in the proximal direction, if done so sufficiently forcefully, will disengage the retainer ring 36 of the tip protector from the retainer depression 58. This will permit the clinician to move the tip protector proximally from the catheter hub 20 without moving the needle 26 relative to the tip protector 34. The tip protector 34 thereby serves to fully shield the sharp and bloodied end of the needle to permit disposal of the shielded needle without risk of inadvertently piercing the clinician's skin.

The invention may be embodied in other specific forms without departing from its spirit or essential characteristics. The described embodiment is to be considered in all respects only as illustrative and not restrictive and the scope of the invention is, therefore, indicated by the appended claims rather than by the foregoing description. All changes which come within the meaning and range of equivalency of the claims are to be embraced within their scope.

What is claimed is:

1. A catheter and insertion needle assembly for reducing the risk of a user from inadvertently piercing their skin with the needle after it has been applied to a patient, the assembly comprising:

a catheter having a proximal end and a distal end;

a catheter hub connected to the proximal end of the catheter for fluid communication therewith;

an insertion needle for disposition within the catheter and catheter hub, the insertion needle having a locking ring disposed securely about the exterior of said needle near the distal end thereof, the locking ring being positioned on said needle so as to permit projection of the distal end of the needle through the distal end of the catheter sufficiently to provide effective penetration of the needle and catheter into the patient's vascular system;

a tip protector comprising a generally cylindrical tube configured so as to be disposed within the catheter hub and so as to be movable axially within said hub, the tip protector including a retainer ring externally disposed thereon and configured to engage a corresponding retainer depression on an internal wall of said catheter hub, said tip protector including a wall at its proximal end with an opening therein sufficiently large to permit the passage of the insertion needle therethrough but sufficiently small to preclude the passage of the locking ring therethrough, and a rigid insert comprising a generally cylindrical collar configured to be disposed tightly within the interior of the tip protector, the insert having a taper at a proximal end so that the interior diameter of the insert at its proximal end is smaller than the interior diameter of the insert at its distal end and smaller than the exterior diameter of the locking ring on the insertion needle, the tapered end of said insert comprising discrete cantilevered sections that may be biased outwardly upon the forced passage therethrough of the locking ring, said insert positioned within the tip protector so as to permit the locking ring to rest in a locked position within the tip protector between the insert and the proximal wall of the tip protector, whereby when the insertion needle is withdrawn from the patient and drawn axially through the catheter and tip protector in the proximal direction, the locking ring passes through the insert and becomes lodged between the insert and the proximal wall of the tip protector so as to substantially prevent further axial movement of the insertion needle, and whereby exertion of additional force on the inserted needle in the proximal direction will force the tip protector to disengage from the catheter hub so that, when the needle is entirely withdrawn from the catheter and catheter hub, the distal tip of the insertion needle is fully shielded within the tip protector.

2. The assembly of claim 1, wherein the catheter comprises a soft material having a hardness of about 70 on the Shore A hardness scale.

3. The assembly of claim 2, wherein the catheter has been treated at its distal end to be harder than the rest of the catheter.

4. The assembly of claim 1, wherein the catheter further comprises an internal shoulder near the distal end thereof and wherein the locking ring is positioned on the needle so that the locking ring abuts the internal shoulder when the insertion needle is fully advanced within the catheter in the distal direction.

* * * * *